United States Patent
Al-Jasim (10) Patent No.: US 10,729,537 B2
(45) Date of Patent: *Aug. 4, 2020

(54) PYRAMID-SHAPED BREAST IMPLANT FOR BREAST AUGMENTATION, BREAST RECONSTRUCTION, OR BREAST LIFT WITH A METHOD OF USE AND PRODUCTION OF THE SAME

(71) Applicant: Apex Medical Device Design LLC, Lynwood, WA (US)

(72) Inventor: Nedaa AbdulGhani Nasif Al-Jasim, Lynwood, WA (US)

(73) Assignee: Apex Medical Device Design LLC, Lynwood, WA (US)

( * ) Notice: Subject to any disclaimer, the term of this patent is extended or adjusted under 35 U.S.C. 154(b) by 49 days.

This patent is subject to a terminal disclaimer.

(21) Appl. No.: 15/911,979

(22) Filed: Mar. 5, 2018

(65) Prior Publication Data

US 2018/0303599 A1    Oct. 25, 2018

Related U.S. Application Data

(63) Continuation of application No. PCT/US2016/047635, filed on Aug. 18, 2016, which
(Continued)

(51) Int. Cl.
*A61F 2/12* (2006.01)
*B29C 41/14* (2006.01)
(Continued)

(52) U.S. Cl.
CPC .............. *A61F 2/12* (2013.01); *B29C 41/085* (2013.01); *B29C 41/14* (2013.01);
(Continued)

(58) Field of Classification Search
CPC ........................................................ A61F 2/12
(Continued)

(56) References Cited

U.S. PATENT DOCUMENTS 4,778,465 A    10/1988 Wilkins
5,112,352 A *   5/1992 Novack ................. A61F 2/12
                                                     623/8
(Continued)

FOREIGN PATENT DOCUMENTS

EP          2161042 A1    3/2010
EP          1515665 B1    2/2012
WO       2010019292 A1    2/2010

OTHER PUBLICATIONS

International Search Report and Written Opinion of the International Searching Authority for PCT Application PCT/US2016/047635 dated Dec. 28, 2016.
(Continued)

*Primary Examiner* — Suzette J Gherbi
(74) *Attorney, Agent, or Firm* — Michael G. Monyok (57) ABSTRACT

The disclosure describes a breast implant device product that mimics the natural pectoral fat of the breast and is characterized by an incomplete pyramid with isosceles triangular base and wedge-shaped edges and sloping faces that meet at acute angles with variable degree located medially, laterally, and on the top and a footprint characterized by a semicircular lower portion and an oval paraboloid upper portion and a center of gravity located closer to the footprint than to the profile, the said footprint is advantageously converging and moving towards the underlying surface as the chest wall with a method of manufacturing and a method of use of the said implant including a breast pyramid sizing system.

16 Claims, 7 Drawing Sheets

Related U.S. Application Data is a continuation of application No. 14/756,492, filed on Sep. 5, 2015, now Pat. No. 9,707,073.

(51) Int. Cl.
 *B29C 41/08* (2006.01)
 *B29K 83/00* (2006.01)
 *B29L 31/00* (2006.01)
 *B29K 105/00* (2006.01)

(52) U.S. Cl.
 CPC ............ *A61F 2230/0008* (2013.01); *A61F 2230/0086* (2013.01); *A61F 2240/004* (2013.01); *A61F 2250/0003* (2013.01); *A61F 2250/0078* (2013.01); *B29C 41/08* (2013.01); *B29K 2083/005* (2013.01); *B29K 2105/0061* (2013.01); *B29L 2031/7532* (2013.01)

(58) Field of Classification Search
 USPC ........................................... 623/7–8
 See application file for complete search history.

(56) References Cited

U.S. PATENT DOCUMENTS

| | | | |
|---|---|---|---|
| 5,236,454 | A | 8/1993 | Miller |
| 5,480,429 | A * | 1/1996 | Weber-Unger ............ A61F 2/52 2/267 |
| 7,105,116 | B2 | 9/2006 | Benin et al. |
| 10,039,633 | B2 * | 8/2018 | Ansorge ................. A61F 2/12 |
| 2002/0038147 | A1 * | 3/2002 | Miller, III ................ A61F 2/12 623/8 |
| 2002/0068972 | A1 | 6/2002 | Weber-Unger et al. |
| 2004/0162613 | A1 * | 8/2004 | Roballey ................ A61F 2/12 623/8 |
| 2005/0027307 | A1 | 2/2005 | Schwartz et al. |
| 2005/0149186 | A1 * | 7/2005 | Roballey ................ A61F 2/12 623/8 |
| 2006/0229721 | A1 * | 10/2006 | Ku .......................... A61F 2/12 623/8 |
| 2006/0282164 | A1 * | 12/2006 | Seastrom ............. A61F 2/0059 623/8 |
| 2008/0161916 | A1 * | 7/2008 | Heitman ................. A61F 2/52 623/7 |
| 2009/0149953 | A1 * | 6/2009 | Schuessler ............. A61F 2/12 623/8 |
| 2011/0245921 | A1 | 10/2011 | Stelter et al. |
| 2012/0004723 | A1 | 1/2012 | Mortarino et al. |
| 2012/0226352 | A1 * | 9/2012 | Becker .................... A61F 2/12 623/8 |
| 2012/0277860 | A1 | 11/2012 | Dvir et al. |
| 2013/0302510 | A1 | 11/2013 | Yu |
| 2014/0163678 | A1 | 6/2014 | Van Epps |
| 2014/0170234 | A1 | 6/2014 | Van Epps et al. |
| 2014/0222146 | A1 * | 8/2014 | Moses .................... A61F 2/12 623/8 |
| 2015/0351900 | A1 * | 12/2015 | Glicksman ............. A61F 2/12 623/8 |
| 2019/0175332 | A1 * | 6/2019 | Schuessler ............. A61F 2/12 |

OTHER PUBLICATIONS

Schwartz, Michael R. "Algorithm and techniques for using Sientra's silicone gel shaped implants in primary and revision breast augmentation." Plastic and reconstructive surgery 134, No. 1S (2014): 18S-27S.

Eaves III, F. F. et al. "Introduction to the Sientra High-Strength Cohesive Gel Implants Supplement." Aesthetic surgery journal 35, No. suppl_1 (2015): S1-S2.

Blondeel, P. N. et al. "Shaping the breast in aesthetic and reconstructive breast surgery: an easy three-step principle." Plastic and reconstructive surgery 123, No. 2 (2009): 455-462.

Blondeel, P. N. et al. "Shaping the breast in aesthetic and reconstructive breast surgery: an easy three-step principle. Part IV—Aesthetic Breast Surgery." Plastic and reconstructive surgery 124, No. 2 (2009): 372-382.

Del Yerro, J. L., et al. "Selecting the implant height in breast augmentation with anatomical prosthesis: the "No. Y"." Plastic and reconstructive surgery 131, No. 6 (2013): 1404-1412.

Nickell, W. B. et al. "Breast fat and fallacies: more than 100 years of anatomical fantasy." Journal of Human Lactation 21, No. 2 (2005): 126-130.

European Search Report for European Application EP16842575.9 dated May 14, 2019.

* cited by examiner

PYRAMID-SHAPED BREAST IMPLANT FOR BREAST AUGMENTATION, BREAST RECONSTRUCTION, OR BREAST LIFT WITH A METHOD OF USE AND PRODUCTION OF THE SAME

CROSS-REFERENCE TO RELATED APPLICATIONS

The present application is a Continuation of application Ser. No. PCT/US2016/047635, filed Aug. 18, 2016, which claims priority to U.S. Non-provisional application Ser. No. 14/756,492, filed Sep. 5, 2015, each of which are incorporated by reference herein in their entirety.

STATEMENT REGARDING FEDERALLY SPONSORED RESEARCH

Not applicable.

BACKGROUND OF THE INVENTION

The invention relates to human cosmetic and reconstructive breast surgery. More specifically, the invention relates to pectoral pad breast implant medical devices, a measurement system, and a method of manufacturing and a method of use of the implant devices.

Breast implant devices are implanted under the breast tissue or under the chest muscle to increase breast size (augmentation) or to rebuild breast tissue after mastectomy (reconstruction). They are also used in revision surgeries, which correct or improve the shape and size of an original surgery or treat complications. Breast implants are additionally used in breast lift surgery.

A breast implant device is manufactured as an outer shell of silicone elastomer (rubber) distended with a fill material that can be either sterile saline solution or silicone gel (for example, fourth generation soft silicone or fifth generation form-stable silicone gel).

Current breast implants can be round-shaped or teardrop-shaped, saline-filled or silicone gel-filled, and they come in many combinations of width, profile, length and volume.

Implant shape is the single most important determinant of how the breasts look after augmentation or reconstruction surgery.

The implant shape is determined by the configuration of the mandrel (form, mold, or mandril) used to manufacture the shell. The mandrel is specifically constructed to create an implant having specific physical characteristics. Round-shaped implants are designed as a compressed sphere and teardrop implants mimic a "mature breast" with volume concentration at the lower part and deficient upper part. Hence, both round- and teardrop-shaped designs are constructed on the physical characteristics of a sphere.

Breast augmentation and reconstruction surgery aims to restore the breast's volume and shape that may have been lost due to weight loss, lactation, or aging that leave the breast envelop empty and saggy. Breast augmentation addresses the following most common concerns: lack of upper pole fullness of the breast, lack of projection of the breast, not enough cleavage, and small breasts disproportionately balanced to the overall figure of a patient.

Figure 1:
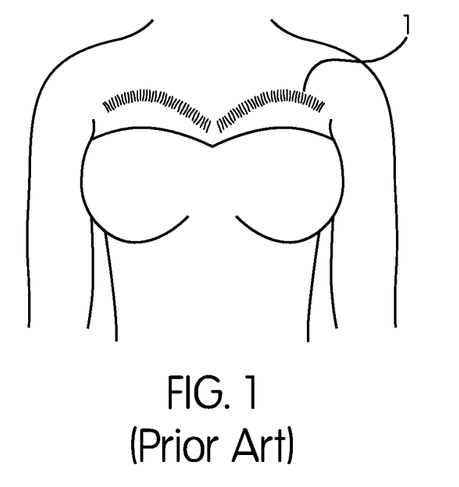
FIGS. 1-2 are illustrations of complications experienced with current breast implant devices.

Studies conducted by breast implant manufacturers under the supervision of regulatory agencies have shown that there are a multitude of common complications that leaves patients unhappy with artificial looking breasts, leading to high incidence of revision surgeries to correct the complications or even to remove the implants without replacement. These complications do not spare even celebrities. Certain defects are shown in the following figures:

FIG. 1 demonstrates wrinkled implant edge 1.

Figure 2:
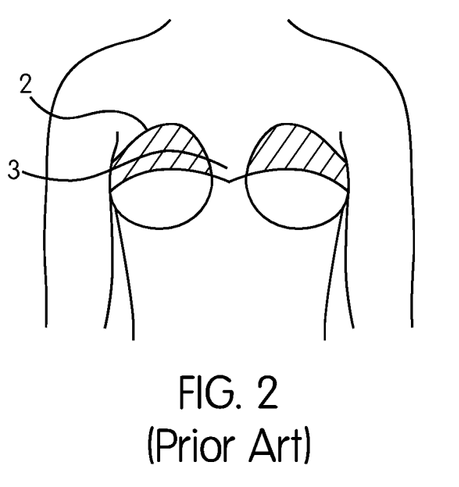

FIG. 2 demonstrates visible implant edges 2, and wide medial cleavage 3.

Figure 3:
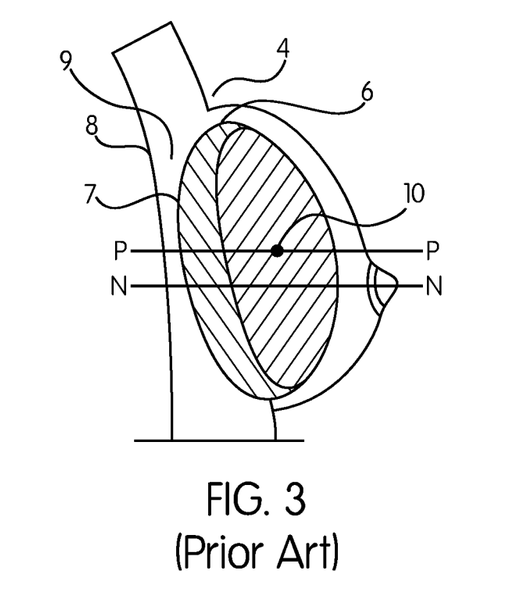
FIG. 3 depicts a lateral view of a round-shaped breast implant depicting a thick, U-shaped upper edge.

FIG. 3 demonstrates a round-shaped breast implant surgically placed behind the breast tissue to demonstrate bulging breast upper pole, with contour break and a step-off transition to the upper chest as a result of using round-shaped implant 4.

Figure 4:
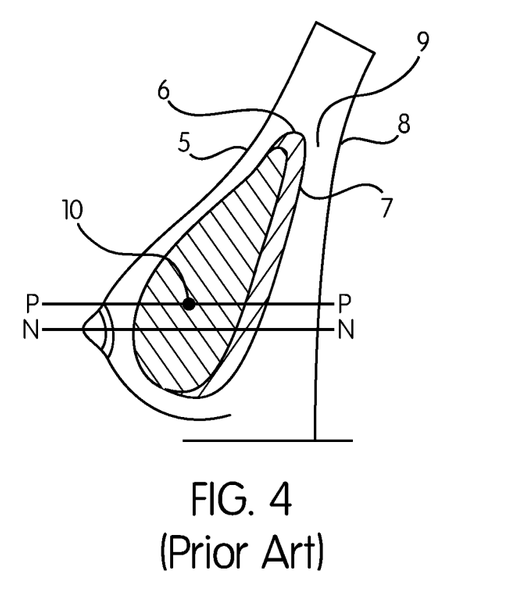
FIG. 4 depicts a lateral view of a current teardrop-shaped implant device.

FIG. 4 demonstrates a teardrop-shaped breast implant surgically placed behind the breast tissue to demonstrate deficient breast upper pole as a result of using teardrop-shaped implant 5.

Figure 5:
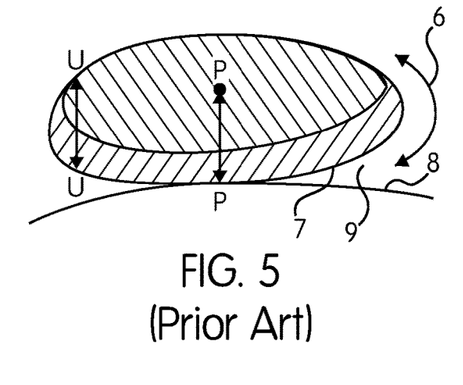
FIGS. 5-6 show current round-shaped and teardrop-shaped implant devices diverging away from the underlying surface.

FIG. 5 demonstrates a round-shaped breast implant placed on a surface.

Figure 6:
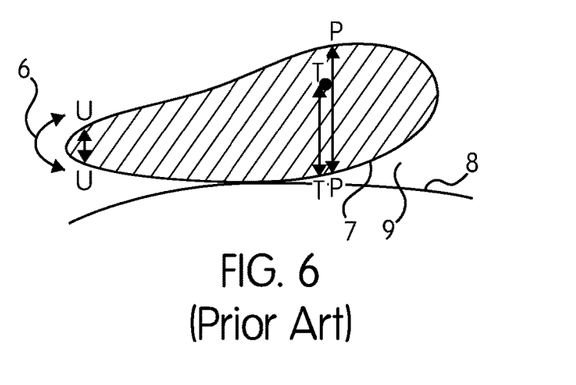

FIG. 6 demonstrates a teardrop-shaped implant placed on a surface.

Many surgeons remain uncomfortable with using teardrop-shaped cohesive-gel textured implants. As such, the main alternative is the traditional round-shaped breast implant.

The market share of teardrop implants is 12.7% of 2955 augmentation cases and 12.3% of 551 reconstruction patients according to one study. Therefore, there is a need for an implant that reduces complications, improves outcomes, and does not require extra technical needs in the hands of all surgeons Fault in Current Implant Design It is important to diagnose the roots of the above-described complications to understand if the complications are the result of faulty implant designs.

FIGS. 3-6 inclusive, demonstrates the multiple faults built in the current implant shape, including:

A. U-shaped thick edges 6 that are visible and palpable. As shown in FIG. 5, the ratio of the thickness of implant projection (profile) (arrow PP) to the edge (arrow UU) in round implants is ½, and in teardrop implant is ⅓. Camouflaging this edge is the primary concern of many surgeons. The present solution is to provide thick tissue coverage by placing the implant under the pectoralis major muscle, injecting homologues fat, or injecting acellular dermal matrix. These solutions help, but do not overcome the problem; hence many women request replacement or removal of the implant.

B. As shown in FIGS. 3 and 6, a convex implant footprint 7 is lying on a concave chest wall 8 and the implant is diverging away from the underlying surface in an angle 9 resulting in a dead space incorporated between the two surfaces, which will eventually become fibrosed, distorting the breast upper pole. In form-stable hard teardrop implants the convex footprint will facilitate rotation, distorting the shape of the breast and creating a major problem that needs revision surgery.

C. Geometric restrictions on implants being sufficiently tall: in a sphere, there is a constant association between volume, width, and height. When a round implant is made taller, it also becomes wider. Often it is wider than what can be accommodated by the breast base. When teardrop implants become taller, they become too narrow to fill the breast from side to side. State-of-the-art teardrop implants are often only be 0.5-1 cm taller than wide as shown in Table 1.

TABLE 1

Dimensions of the state-of-art breast implants with a
difference between the width and vertical height of 0.5-1 centimeters.

| Breast implant style | Width (cm) | Height (cm) | Difference (cm) |
|---|---|---|---|
| Allergan Natrelle ® 410FF (Full height full projection) | 9.5-15.5 | 10-16 | 0.5 |
| Mentor MemoryShape ® CPG ™ Cohesive II, tall height, moderate projection | 9-51.5 | 9.2-15.9 | 0.2-0.4 |
| Sientra HSC+ classic base, moderate profile | 9.5-13 | 10.5-14 | 1 |
| Eurosilicone The Matrix TMF1, TMF2, TMF3 full height | 9.5-15.5 | 10-16 | 0.5 |

D. Referring again to FIGS. 3, 4 and 6, the "center of gravity" 10 of the implant 11 is situated a large distance TT from the chest wall resulting in strong gravitational pull on the implant leading to implant ptosis.

Figure 7A:
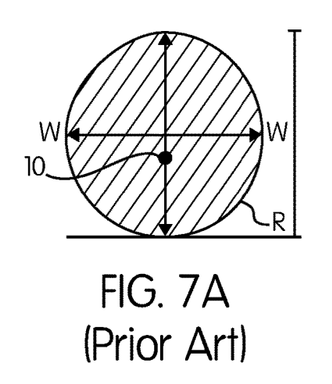
FIGS. 7A-7C are profile views of different current implant devices.
Figure 7B:
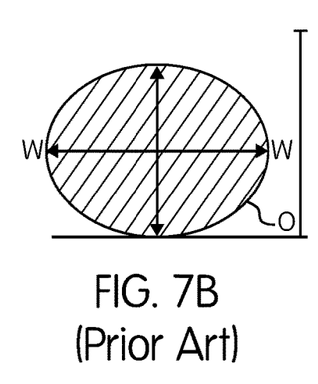
Figure 7C:
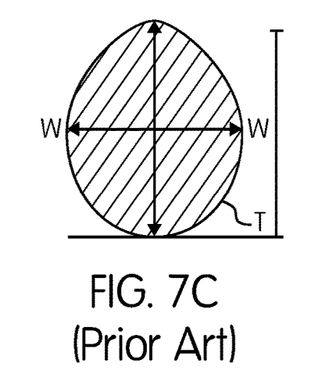

E. The implant footprint does not match the breast footprint, as shown in FIG. 7, where the current teardrop-shaped implant footprints are classic (round) R, oval O with a width bigger than the height, or tall T, while the breast footprint is paraboloid, as will be described later.

Figure 8:
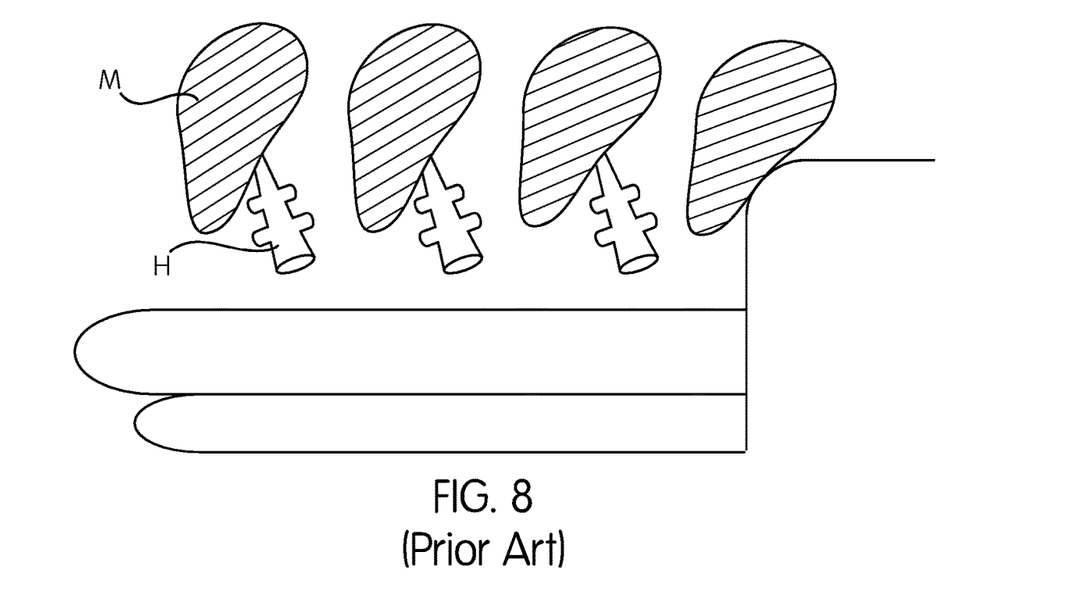
FIG. 8 is an illustration of the current manufacturing method.

The current method of manufacturing a teardrop breast implant is shown in FIG. 8, where a teardrop shaped mandril M is inserted to a rotating machine via its handle H.

Similar complications and design problems involve implants used to augment or replace the gluteal area (buttock), facial check, calf, testes, and other body parts. Therefore, it would be beneficial to design an implant that overcomes these design flaws.

BRIEF SUMMARY

In one embodiment, the implant device comprises a non-spherical shaped device that mimics breast fatty tissue, which gives a natural breast its volume, shape, and proportions. In yet another embodiment, the non-spherical shape is an isosceles oblique triangular pyramid with V-shaped edges. Further, the implant vertical height is free from correlation to the width. In yet another embodiment, the implant device comprises a converging footprint that lies on the convex chest wall. The paraboloid footprint is similar to natural breast footprint.

In some embodiments, the volume distribution of the implant device is mainly on the central portion close to the footprint, and the "center of gravity" is located near the chest wall, helping the implant to resist gravitational pull.

It is a goal of the pyramid-shaped implant design to: improve on aesthetic outcomes of surgery; overcome problems associated with the current state-of-art implants; and defy gravitational pull on the implant.

Improvement on aesthetic outcomes includes a direct extension of the implant to fill the breast upper pole resulting in a slanted outer look, ample medial cleavage, spontaneous nipple placement of the implant profile, and proportionate upper breast to lower breast fill of 45:55 percent, according to one embodiment. Overcoming the problems of visibility and palpability are built in a design with wedge-shaped edges and the wedge is naturally wrinkle-free. Defying gravitational pull on the implant by relocating the implant center of gravity.

Prevention of implant displacement is achieved by designing a lateral wing that extends into the axilla to fix the implant in position.

Another aspect of the present invention is a method of manufacturing the implant, which comprises in one embodiment: 1—manufacturing a 3-dimensional mandrel that mimics the configuration of breast fatty tissue, including sculpturing the implant mold to an adult women breast shape, adding a segment of a sphere to form the shape of the breast lower pole, creating a family of molds with different dimensions and volumes to meet the needs of different women, locating the implant center of gravity, 2—adding a handle to the mandrel for attachment to a rotating machine, 3—dipping the mandrel repeatedly into non-polymerized silicone gel to form the implant shell, 4—curing the shell and separating it from the mandrel, and 5—filling the shell with saline solution or silicone gel.

Other embodiments of the manufacturing process include: manufacturing pre-operative implant sizers with the same physical characteristics of the implant mandrel; manufacturing intra-operative implant sizers with the same physical characteristics of the implant mandrel; and manufacturing intra-operative tissue expanders with the same physical characteristics of the implant mandrel.

According to one embodiment of the invention, a method of use of the implant includes: 1—pre-operative implant size selection, 2—intra-operative creation of surgical pocket to receive the implant, and 3—intra-operative implant sizing or tissue expanding Pre-operative implant sizing is related to choosing the right implant size and dimensions for a particular women to achieve her desired outcomes. Specific pre-operative sizing for the implant of the pyramid-shaped breast implant is based on the dimensions and equations of the breast pyramid.

Manufacturing implant surgical devices for other parts of the body as the buttock or face with wedge-shaped edges, flat footprint, and fixation holes to improve on surgery outcomes and overcome complications

DETAILED DESCRIPTION

Figure 9:
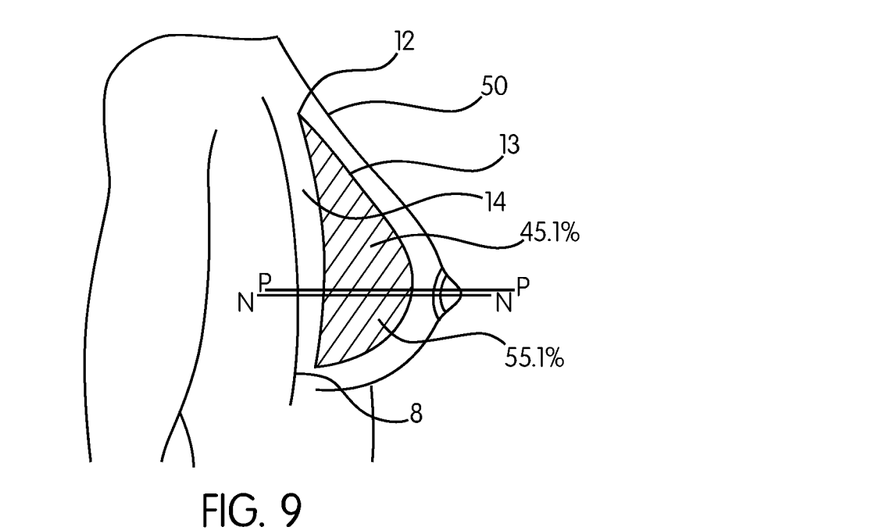
FIG. 9 is a lateral view of the breast implant device, according to one embodiment.

In reference to FIG. 9, a pyramid-shaped breast implant 11 is shown in accordance with one embodiment of the present invention. The breast implant 11 is a non-spherical shape, but rather mimics a triangular pyramid with an inverted V-shaped apex 12 to overcome implant visibility and palpability, and straight anterior slope 13 to provide appropriate size and shape to the breast upper pole with a wrinkle-proof character. The implant footprint 14 is diverging towards the chest wall. Further, in this embodiment depicted in FIG. 9, the implant profile line PP coincides with the nipple line NN for easy positioning of the nipple. In addition, along the line PP is the implant "center of gravity" 10, which is located closer to the chest wall to provide gravity defying properties.

Figure 10:
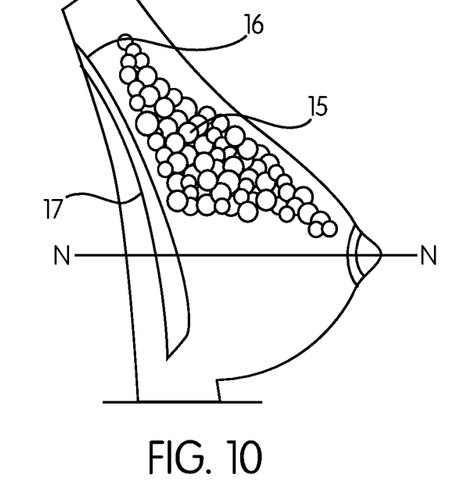
FIG. 10 depicts breast fatty tissue.

The implant 11 is designed to mirror the structure and configuration of breast fatty tissue 15, which is depicted in FIG. 10. The breast mound shape, volume, and general perkiness are attributed to breast fatty tissue 15, herein referred to as "pectoral fat" 15. The physical characteristics of pectoral fat 15 are that of a truncated triangular pyramid with obtuse isosceles triangular base.

Gross Anatomy of Pectoral Fat

Referring again to FIG. 10, depicted in the illustration is a sagittal section of the pectoral fat 15 of the breast at the nipple level NN that fills the skin envelop, extending upward to the second rib 16, encasing the milk glands, padding the pectoralis major muscles 17, and shaping the breast upper half.

Figure 11:
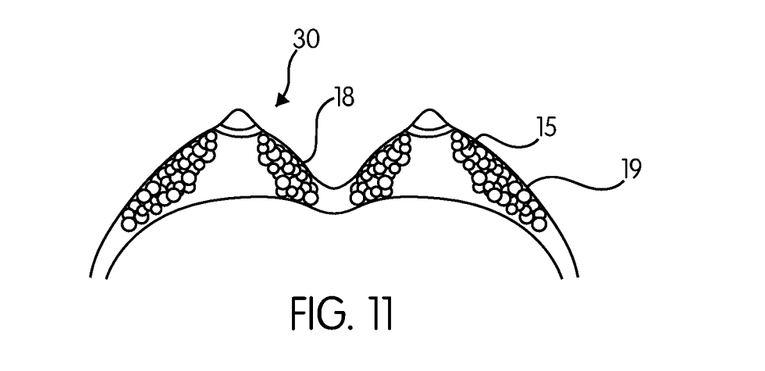
FIG. 11 is an overhead view of breast fatty tissue.

FIG. 11 depicts a transverse section of the breast at the nipple level to demonstrate that the pectoral fat 15 is shaping the breast medial cleavage angle 18, which is about 80° degrees, and shaping the lateral axillary angle 19 similar to a V-shaped edges.

Figure 12:
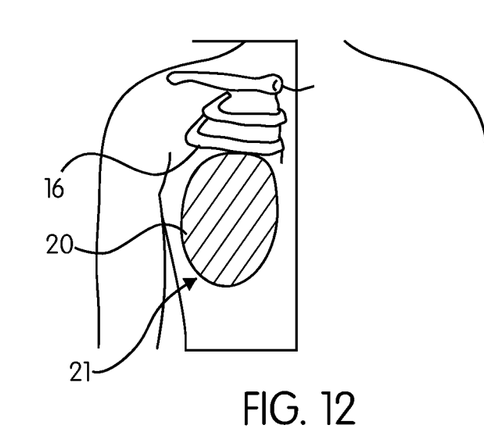
FIG. 12 depicts the breast footprint on the chest wall.

FIG. 12 further demonstrates that pectoral fat 15 forms the breast footprint 20 which is defined as the foundations on which the breast sits on the chest wall with its boundaries 21 having a paraboloid shape.

Configuration of Pectoral Fat

Figures 13, 14:
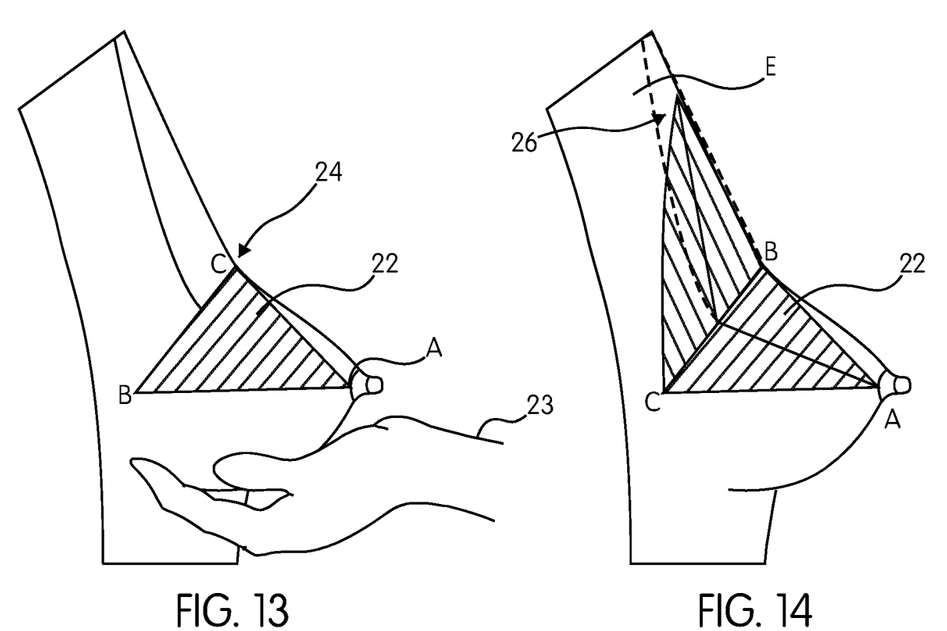
FIGS. 13-14 show the measurement of a breast upper-pole.

Pectoral fat 15 is configured in the shape of a triangular pyramid that will be referred to as the "breast pyramid" with an obtuse isosceles triangular base that will be referred to as the "breast triangle", and are demonstrated by the following figures:

FIG. 13 demonstrates how to draw the base of the pyramid wherein a standing woman holds her breast lower part 22 by her cupped hand 23 and pushes it up until a bend-angle 24 will be formed at the junction of the breast lower and upper parts. In this position, a triangle is drawn on the skin with its vertex located at the nipple 25, and the base located at the bend-angle 24, this resultant obtuse isosceles triangle ABC, forming the "breast triangle". Line BC represent the breast base width. The median of the triangle AD (as shown in FIG. 14) represents the breast profile (maximum forward projection), and the maximum stretch of the nipple. The surface area of the breast triangle is calculated by the following formula: ½ base×height. The breast triangle forms the base of the breast pyramid.

FIG. 14 demonstrates the method of visualizing the apex E of the pyramid ABCE in a sleeping position, where the woman is asked to gently push the breast towards the rib cage and the uppermost visible boundary 26 of the breast is marked. Alternatively it is marked at the level of the sternal angle. The vertical height of the triangular pyramid is line DE. The footprint of the pyramid is the triangle BCE, in addition to the bottom segment that will be described later. The two lateral faces are triangular in shape ABE and ACE, that meets at the anterior (front) edge AE. The volume of the triangular pyramid is calculated by the following formula: ⅓×base area×height DE.

Figure 15:
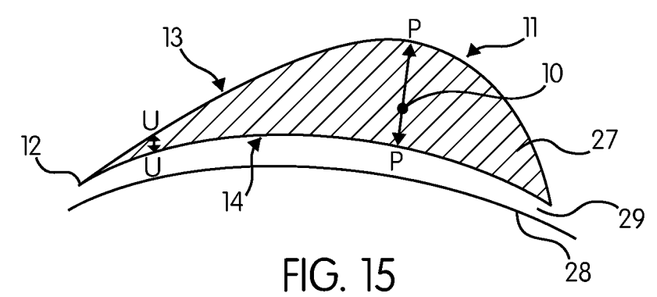
FIG. 15 is an illustration of the contoured footprint of the implant device, according to one embodiment.

Referring to FIG. 15, in one embodiment the implant bottom portion 27 is in the form of quarter segment of a sphere, having a diameter that is equal to the breast base width BC to smoothly fill the breast lower pole. The volume of this portion is calculated by the formula: ¼×[(4/3) pi r³, wherein r is DC. The breast pyramid vertical height joins the infra-mammary line at the point F. According to this embodiment, the final implant shape is formed and is sculptured to resemble a natural breast shape. Given the pyramidal dimensions, the implant is referred to as a pyramid-shaped breast implant.

Physical Characteristics of Pyramid-Shaped Implant

The physical characteristics of pyramid shaped implant 11 are described by referring to the figures:

Referring again to FIG. 9, the shape of the implant 11 in situ under the breast tissue is depicted. The implant increases the volume and improves the shape of the breast.

FIG. 15 is a lateral view of the implant 11 placed on a surface 28, with its longitudinal section characterized by V-shaped thin edge at the apex 12. The ratio of the thickness of implant projection (profile) line PP to the edge thickness line UU is ⅕ or less. FIG. 15 further demonstrates the implant 11 bottom 27, with an acute angle about 80 degree. FIG. 15 also demonstrates a relaxed implant footprint 14 that is moving toward (converging) the underlying surface 28 and meets the surface at a small convergent angle 29 of about 0-5 degrees. FIG. 15 further demonstrates a straight-sloped, wrinkle-free frontal edge 13.

FIG. 15 further demonstrates that in this embodiment, the implant 11 is freed from the vertical height to width relationship, thus enabling the implant to be 3-6 centimeters taller than wide (see, for example, Table 2). In this embodiment, the ratio of the vertical height above the profile arrow PP to below the arrow PP is 2×/1×. As shown in the implant 11 in FIG. 15, the implant 11 center of gravity 10 along the profile line PP is closer to the chest surface 28.

Figure 16:
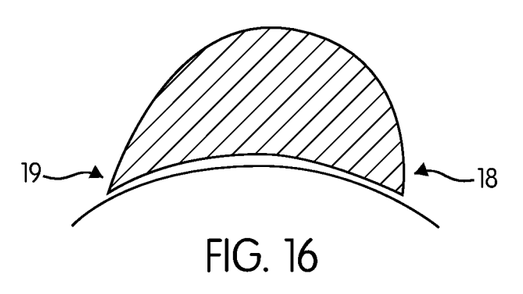
FIG. 16 is another view of the implant device according to one embodiment of the present invention.
Figure 17:
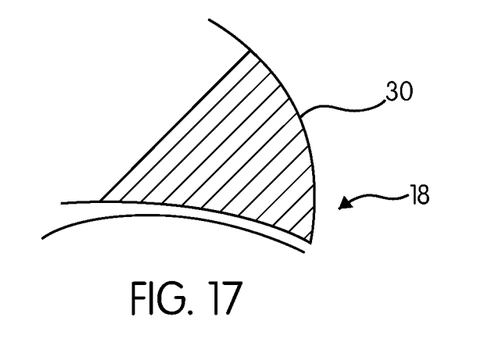
FIG. 17 shows the edges of an implant device according to one embodiment.

FIG. 16 is a cross section of pyramid-shaped breast implant 11, as viewed from the top, demonstrating medial cleavage angle 18 and lateral axillary angle 19. Angles 18 and 19 can be different, allowing an improvement in medial cleavage. FIG. 17 shows a closer look at the adjustable medial cleavage angle 18 that can reach up to 85°, with a sculptured medial surface 30.

Figure 18:
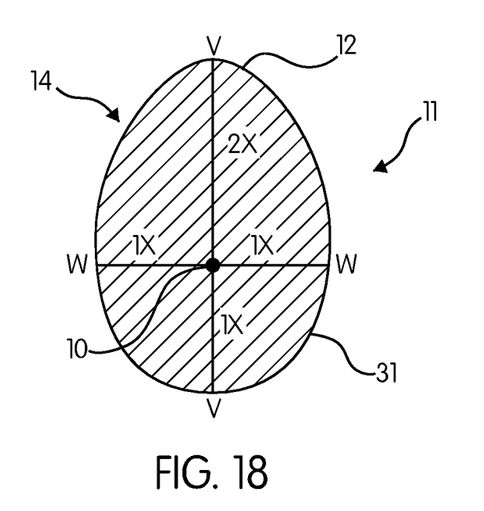
FIG. 18 is a profile view showing the relative dimensions of the breast implant device footprint.

FIG. 18 demonstrates implant 11 footprint 14 with its apex 12, and paraboloid boundaries 31. The boundaries 31 are similar to the breast footprint 20 shown in FIG. 12, which provides superior aesthetic results from augmentation and reconstruction surgical procedures. With spherical implants, the footprint is circular.

FIG. 18 further shows the dimensions of implant 11, where the transverse line WW marks the implant width (2×), intersecting with the implant line VV marking the vertical height (3×), dividing the implant 11 into upper ⅔ and lower ⅓ portions.

In some embodiments, implant 11 is described as a "defy gravity" implant because its center of gravity 10 has been relocated closer to the chest wall 28, as demonstrated in the following figures. Referring again to FIG. 15, the center of gravity 10 is located along the profile line PP closer to the implant footprint than the top of the implant 11 when viewed laterally. FIG. 18 demonstrates implant 11 footprint 14 with its center of gravity 10 located at the intersection of the transverse line WW and the vertical line VV.

Figure 19:
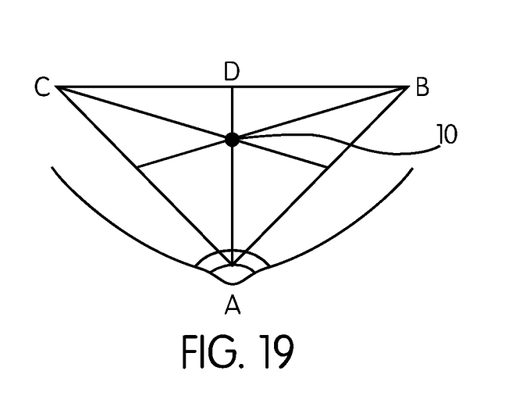
FIG. 19 shows different calculations for implant sizing.

FIG. 19 demonstrates the center of gravity 10 of the breast triangle (points ABC), corresponding to the centroid located at the intersection of the three medians of the breast triangle, at about two-thirds of the way along each median closer to the baseline BC. Hence, the center of gravity 10, also known as the "center of mass", has been moved in the implant 11 closer to the implant footprint and the chest wall.

By moving the center of gravity 10 of the implant 11 closer to the chest wall, the implant 11 will be better supported by the natural breast tissue. For example, a vertical line extending downward from the implant center of gravity 10 falls near the infra-mammary tissues. As a result, the implant 11 will be supported by the breast tissue to minimize the downward gravitational forces on the implant 11.

Method of Manufacturing Pyramid-Shaped Breast Implant

The configuration of the mandrel used to manufacture the implant 11 is created taking into consideration the above-described physical characteristics of pectoral fat 15, the breast triangle ABC (see FIG. 13), breast pyramid ABCE, the physical characteristics of the breast pyramid ABCE, the implant bottom portion as demonstrated in FIGS. 15-18, and the location the center of gravity 10.

For example, in one embodiment, the outer shell of a pyramid-shaped implant 11 is manufactured by using a specifically-shaped mandrel as the inherent shape of the implant outer shell is determined by the physical characteristics of the mandrel. As the foregoing disclosure indicates, the implant mimics the fatty tissue of the breast. As such, in one embodiment, the mandrel also mimics the physical characteristics of the fatty tissue of the breast (pectoral fat) 15. In an alternative embodiment, the mandrel mimics the physical characteristics breast pyramid ABCE. A person having skill in the art will appreciate that the ultimate dimensions of the implant 11 and mandrel are based on the measurements of the patient for which the implant 11 is being created. Thus, the measurements will vary depending on the application. Some examples of the dimensions of the pyramid-shaped implant 11 are shown in table 2.

TABLE 2

Examples of pyramid-shaped breast implant dimensions

| Implant volume CCs | Height cm | Width cm | Profile cm |
|---|---|---|---|
| 195 | 15.2 | 10.2 | 2.3 |
| 250 | 16.5 | 10.5 | 2 |
| 300 | 17 | 11 | 2 |
| 300 | 17 | 9.5 | 2.5 |
| 320 | 15.5 | 10.5 | 3.2 |
| 350 | 17 | 11.5 | 2.5 |
| 400 | 18 | 11 | 3.5 |
| 500 | 18 | 12 | 3.5 |

Figure 20:
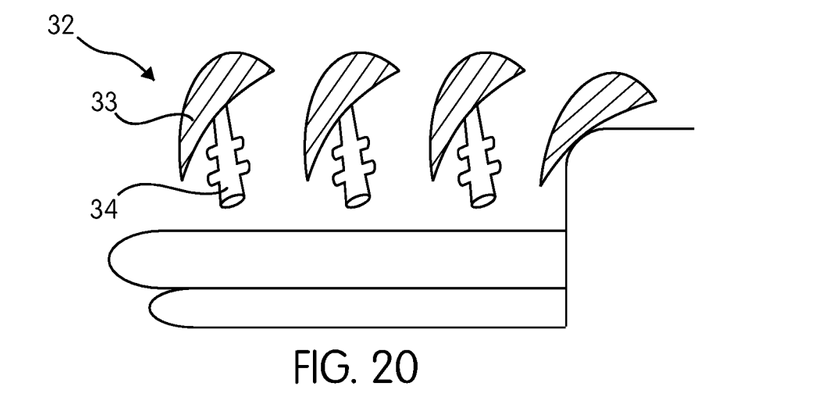
FIG. 20 depicts the manufacturing process according to one embodiment.

FIG. 20 demonstrates the shape of the implant mandrel 32 with a body 33 and a handle 34 that will be attached to a rotating machine. FIG. 20 further demonstrates the appearance of a pyramid-shaped mandrel 32, showing some of the physical characteristics of the mandrel 32 that mimic the breast implant 11, such as the wedge-shaped edges 12 and the flat footprint 14. The mandrel 32 is coated with un-polymerized silicone solution by being dipped into liquid un-polymerized silicone or by other methods known in the art. In other embodiment, the silicone is poured on the mandrel 32 while the mandrel 32 rotates to ensure a uniform thickness of the silicone. Coating the mandrel 32 with silicone is repeated until the desired thickness of the silicone layers is formed.

After coating the mandrel 32 with silicone, the shells are polymerized in an oven. The elastic shell of the implant 11 is stretched and pulled from the mandrel 32. Next, the shell is sealed with a patch where the handle 34 connected the mandrel 11. Then, a valve is added to the patch. The valve can be multi-channeled to fill different compartments with the specified fill volume. A person having skill in the art will appreciate that other manufacturing techniques can be utilized.

As previously stated, the configuration of the shell is determined by the shape and dimensions of the mandrel 11. As such, various shapes of mandrels 11 are created, with the shape being dependent on implant vertical height, implant footprint width, and implant profile, among other shape considerations. However, the implant dimensions are not a limiting factor for this invention. For example, in one embodiment, the medial cleavage angle 18 is varied in any range from 30-89, preferably 60-80, with a curved medial face 30, as shown in FIG. 11.

Another variable in the implant design that influences how the implant will perform in a patient is the composition of the material used to fill the implant shell, giving it volume. The fill material can be sterile normal saline solution, $4^{th}$ generation cohesive silicone gel, $5^{th}$ generation highly cohesive form-stable silicone gel, or any other fill material known in the art with safety and suitability for use in humans. In another embodiment, the implant 11 can be manufactured as a three-dimensional shape without the need for a shell and a fill, just a pliable pyramid-shaped silicone implant. In yet another embodiment, different types of fills can be used in different compartments within the shell of the implant 11.

In yet another embodiment, the implant is pre-filled with silicone gel, while in other embodiment the implant can be filled intra-operative (during operation) with normal saline solution. Generally, the type and distribution of the implant fill is not a limiting factor for the invention.

In one embodiment the footprint of the implant 11 can be fortified by increasing the thickness of one layer or more of the implant outer shell. The thickening can take the shape of interlocking "C"s, a cross, or a rim around the edges to maintain the implant vertical height and/or to prevent rotation.

Some embodiments of the implant 11 can have hole at the peripheral edges of the implant 11 or an attached ring that can be used for surgical fixation of the implant to the overlying breast or underling chest tissues. However, it is unlikely that a pyramid-shaped implant 11 will have a tendency to be displaced. Certain mechanics of the design to keep the implant 11 in place, including:

Wedge mechanics—the implant edges can be pushed "to-the-point", hence are fixed in place under the narrow origins of pectoralis major muscle. Pectoralis contractions will have a mechanical fixing effect by pressing the implant towards the breast footprint.

Relaxed implant footprint converging on the rib cage fits like a hand-in-glove inside the surgical placement pocket, creating an air-tight room that hold the implant in situ against gravitational pull and against rotational forces.

Optionally, if the mechanics are not sufficient, i.e., big implants, surgical fixation is an option.

Implant Fill Relocation

The implant 11 has a thin periphery and a thick center, whereas prior art implants have a thick periphery and a thick center. As a result, the implant fill distribution has been relocated as an outcome of the pyramid-shaped design. In one embodiment, the implant fill volume is distributed according to the aesthetically desirable upper part volume: lower part volume ratio of 45:55, divided by a transverse line passing at the level of the highest point (implant profile).

A unique equation for calculating implant volume distribution percent is incorporating existing breast tissue volumes in the calculation. The percent distribution equation is following: existing breast upper pole volume+implant upper part volume/45=existing breast lower pole volume+implant lower part volume/55.

Figure 21:
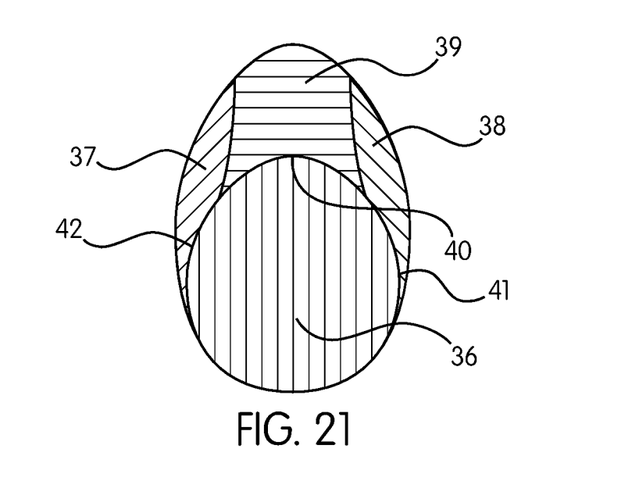
FIG. 21 shows implant fill distribution and internal septa.

FIG. 21 demonstrates the fill distribution, according to one embodiment, wherein the footprint of the implant is sculptured to resemble the human hand, with a central round palm area 36 having 55% of the total volume to be placed behind the nipple-areolar complex, with two wings (lateral axillary 37 and medial cleavage 38) with a volume of 20% of the total, and an upper extension 39 with a volume of 25% of the total. FIG. 21 shows the implant footprint with volume distribution percentage. The resultant shape resembles a round-shaped implant with wings. This volume distribution can be achieved through internal septa according to the hand lines 40, 41, and 42 of FIG. 21. In one embodiment, the volume distribution is achieved by using form-stable silicone gel.

Figure 22:
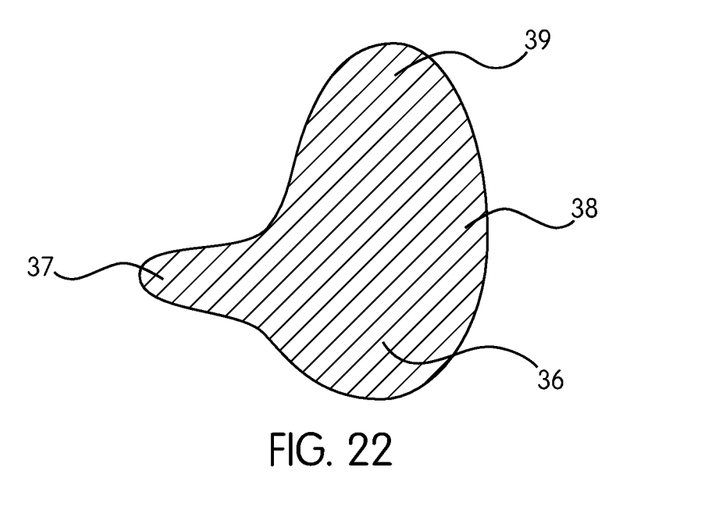
FIG. 22 shows implant lateral axillary wing.

FIG. 22 demonstrates an alternative embodiment wherein the lateral axillary wing 37 is extended to the axilla to provide additional volume in this area or to provide better fixation of the device.

Method of Using Pyramid-Shaped Breast Implant

The surgical use of the implant 11 of the present invention can be based on decisions shared between the surgeon and his patient related to the choices of the implant device and the surgical steps. Several of the steps are common to those known in the art, but some steps are specific to the pyramid-shaped implant 11.

The method of use of implant 11 include the following steps:

VI. Pre-operative implant sizing
VII. Selecting implant specifications
VIII. Intra-operative implant sizing
IX. Operative procedure options
X. Post-operative assessment of implant effectiveness
I. Pre-Operative Implant Sizing The Specific pre-operative implant sizing system for the pyramid-shaped breast implant 11 is referred to as the "Breast Pyramid System" and is used to address one of the most critical decisions before going to surgery: implant size. Implant size selection process is about choosing the right implant size that is suitable for a particular patient anatomy and is used as part of establishing a definitive operative plan.

The system consist of multiple consecutive steps, including:

Measuring the patient's breast dimensions. In one embodiment, the measurements incorporates vertical height DE of the breast pyramid shown in FIG. 14, in addition to base width BC, and the breast profile AD of the breast pyramid ABC of FIG. 13. The volume of the implant above the nipple line is then calculated. The total implant volume is then calculated as the volume of the breast pyramid+ volume of the lower segment 27 (seen in FIG. 14).

In an alternative embodiment the full height of the breast footprint is measured from the pyramid top E to the point F at infra-mammary line. Then the implant volume is calculated using the following patient input: implant 11 height EF, implant 11 base width BC, and implant 11 profile AD are input into a "Breast Pyramid Chart," that is specifically formulated for the purpose of using pyramid-shaped implant 11. The chart enables the conversion of the breast dimensions into an implant volume, such as cubic centimeters, for example.

Within the chart, implants 11 are grouped into product cells, each with unique heights and projection ratios that extend across a range of base widths to meet the needs of different patients and deliver the results expected by the surgeon and patient. In an alternative embodiment, the chart product cells use implant heights and base width ratios that extend across a range of implant profiles.

In one example embodiment, the implant 11 range of measurement includes a vertical height range of 10-18 cm (increasing by 0.5 cm each), a profile range of 2-6 cm (increasing by 0.2 cm each), a width of 8-16 cm (increasing by 0.5 cm each), and a size range of 150-800 cc's (increasing by 25 cc's each). The dimensions of the implant 11 are not a limiting factor for this invention.

When the sizing process is complete, the surgeon has a narrow size range that will be considered for surgery. For example, the surgeon might have two options. This gives the surgeon some latitude during surgery to make the best judgment based on operative conditions.

In some situations, patient contribution in the implant size selection process is considered. The patient can try on pre-operative external implant sizers to have an idea of the volume of implant 11 the patient wants before surgery. In this situation, a pre-operative external sizer can be manufactured with the same specification and configuration as the selected implant 11. Additional sizers can be provided so the patient can determine which size she likes better. Hence, she has experienced a simulation of the final results of the appearance of the implant 11 in clothes before surgery.

Most patients express their desired outcome of surgery by a change in bra cup size. Therefore in one embodiment the sizing system provides a "Cup Size Calculator chart" to determine the implant 11 size that will bring the patient current bra cup size to the desired bra cup size.

In another embodiment, the system provides a three-dimensional surface-imaging program to show the patient photographs with an implant size simulation, demonstrating the changes in the breast volume and contour provided by the implant 11. The program is a simple and useful computational tool for pre-operative breast augmentation planning.

II. Selecting Implant Specifications

The medial cleavage angle created by the implant 11 can be customized by the surgeon according to his aesthetic eye, considering the patient anatomy, and by consulting the patient about her desires and goals for the surgery. Thus, the angle of the implant 11 on the medial cleavage can be included as one specification of the implant 11.

Another specification is whether the shell will have a smooth or textured surface.

Another specification is whether the fill material will be saline or silicone fill material.

Yet another specification is whether to fortify the implant footprint to maintain the vertical implant position or to prevent rotation.

II. Intra-Operative Implant Sizing

During surgery, the surgeon might need to reevaluate the implant size selection according to his operative judgment. To achieve this, the surgeon needs an intra-operative implant sizer that matches the footprint (vertical height and width) of the implant 11. Intra-operative implant sizers can be filled with silicone and are reusable and sterilized or the implant sizers can be filled with saline solution for single use, where the saline sizers come with a fill valve and fill tubes.

IV. Operative Procedure Options

Choices of Surgical Procedures include what type of general anesthesia to use, the manner of making the surgical incision (which are known in the art), and whether pocket placement should be subglandular or submuscular. In one embodiment, the dissection of the surgical pocket can be non-invasive as there is no need for extensive release of the pectoralis major origins as the implant bottom is small and can be easily accommodated in a smaller surgical pocket.

Figures 23, 24, 25:
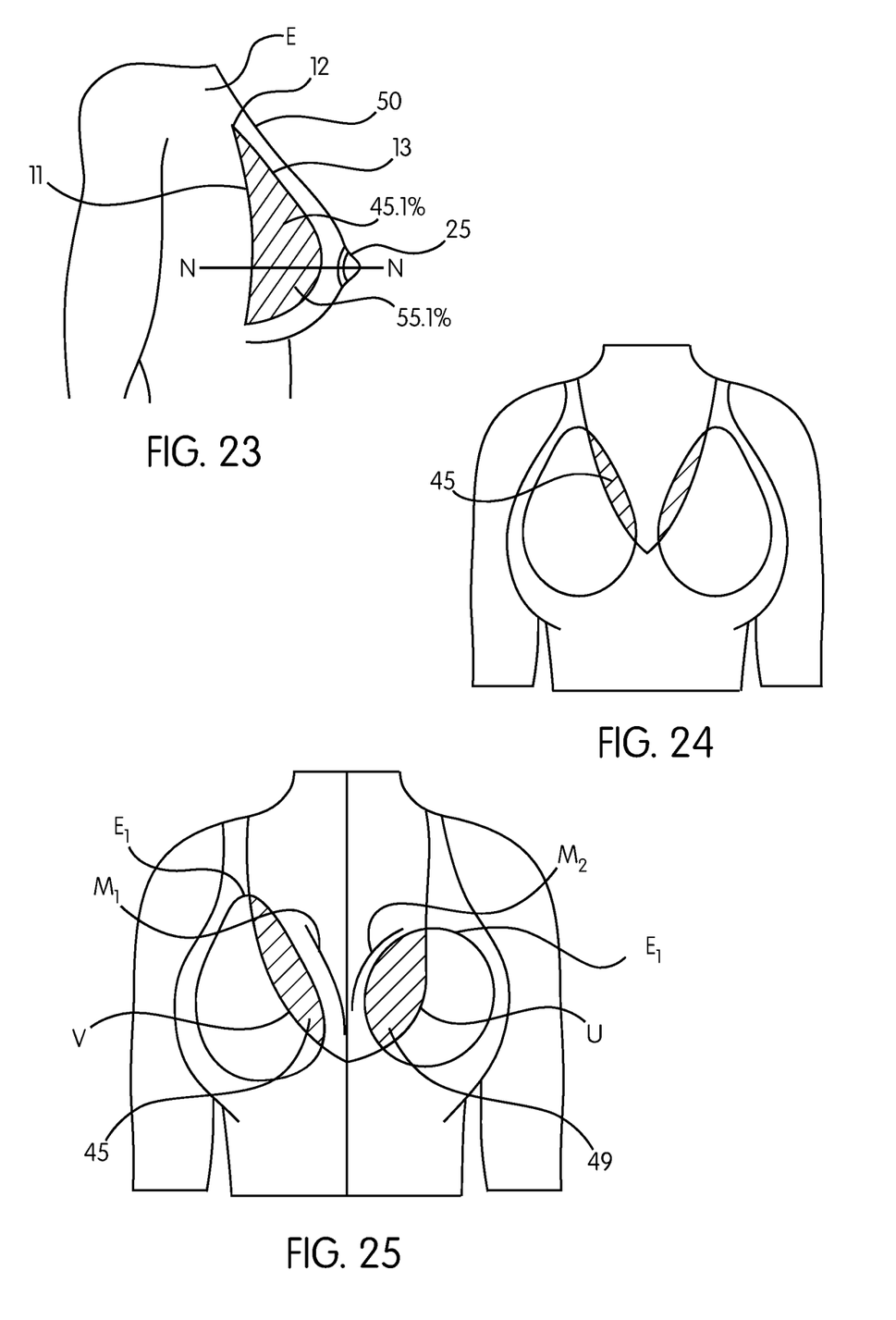
FIGS. 23-25 show the implant device according to one embodiment and its effect on the shape of the patient's breast.

Referring again to the figures, FIG. 23 shows the top of the surgical pocket, where the pocket is dissected upward to reach the upper boundaries of the breast footprint shown in FIG. 18. In one example embodiment, the center of mass PP of the implant 11 is placed behind the nipple-areola 25 complex. The implant axillary wing 37 (as shown in FIG. 22) is inserted into the axilla for increased fill in that particular area and for implant fixation. In another embodiment, the implant 11 can be fixed by suturing holes located at the implant edges to the overlying or underlying tissues.

V. Post-Operative Assessment of Implant Effectiveness

The aim of post-operative assessment of implant effectiveness is to demonstrate that the pyramid-shaped breast implant 11 delivers the aesthetic results for which it was designed.

Post-operative assessment includes two studies: Proof-Of-Concept study, followed by a comparative study comparing the outcomes of using pyramid-shaped implant vs. PURLZ™ commercially available implant sizer 49, which is shown in FIG. 25. The PURLZ™ breast implant sizer 49 is shaped like a round implant and is available in different sizes. The sizer 49 is commercially available from www.l-wgatz.com.

Methods used in both studies assessed the functional performance of the implant 11 by measuring the changes in the breast volume and visualizing the aesthetic changes in the breast contour that resulted from placement of an implant sizers 45 shaped like the implant 11 of the present invention and a PURLZ™ sizer 49 into a bra cup. The results, which show gain in bra cup size, increase in bust circumference around the fullest part of the chest at the nipple level, and the increase in above-bust measurement at the level of the axilla, are shown in Table 3.

TABLE 3

Results of proof-of-concept of pyramid-shaped breast implant study.

| Implant Size | Gain in Cup Size | Increase in Bust Circumference | Increase in Circumference Above Bust |
|---|---|---|---|
| No Sizer | B | — | — |
| 300 cc | B to C | 1 cm | 4 cm |
| 350 cc | B to D | 2.5 cm | 4.4 cm |
| 500 cc | B to D | 3 cm | 6 cm |
| 550 cc | B to DD | 4 cm | 6.8 cm |

According to results in Table 3, the gain in bra cup size that results from implant 11 is more than what is known in round- or teardrop-shaped implants, where an average 200 cc implant increases one cup size, while a 350 cc pyramid-shaped implant 11 results in a gain of two cup sizes and a 550 cc implant 11 results in a gain of three cup sizes.

Further, the increase in above-bust circumference is a unique outcome resulting from implant 11. This increase is an outcome of the pyramid-shaped implant reaching directly to fill the breast upper pole, where round and teardrop-shaped implants that ends abruptly below this level.

FIG. 23 depicts avoidance of a contour break with a slanted takeoff of the breast upper pole 50 from the chest wall, provided by a straight anterior slope of implant 11, which creates a natural-looking breast augmentation. Further, FIG. 23 depicts that the aesthetic ratio of breast upper to lower pole (in relation to the nipple line NN) of 45:55 can be achieved using pyramid-shaped implant 11.

FIG. 24 is an anterior view of the woman depicted in FIG. 23, showing the cosmetic improvement provided using pyramid-shaped implant 11. The woman wears a body-tight top and inserts a 350 cc implant on both sides. It is noticeable that the implant device is smoothly meeting the surrounding tissue, provides a desirable increase in tissue thickness for the upper breast (padding), produces ample cleavage, and maintains a V-neckline of the top.

FIG. 25 shows the comparison between the pyramid-shaped implant sizer 45 and the PURLZ™ implant sizer 49. In this comparison, a woman wears a tight-fitting top and inserts a 300 cc pyramid-shaped sizer 45 on her right breast (left side of figure) and commercial 300 cc Purlz sizer 49 on her left breast (right side of figure). The upward reach of pyramid-shaped implant (arrow E1) is much higher than PURLZ (arrow E2). Further, the medial cleavage of the pyramid-shaped implant (arrow M1) is narrow and ample, whereas the PURLZ sizer 49 creates wide cleavage (arrow M2). Stated differently, the breast configuration with the pyramid-shaped implant 11 is large and perky maintaining the V-neck shape as compared to a sagging contour widening the V-neck of the top. Table 4 shows the results of the comparison.

TABLE 4

Results of Comparative Study

| Criteria for Comparison | Pyramid-shaped Sizer | PURLZ ™ Sizer |
|---|---|---|
| U/L ratio | 45:55, highly desirable | Bulky lower pole |
| Medial cleavage | Ample, highly desirable | Wide apart |
| Breast size and configuration | Perky breast | Droopy breast |
| Compatible to breast footprint | Compatible | Non-compatible |
| V-neck of the shirt | Maintained | Wide U-shaped |

In addition, the physical characteristics of a pyramid-shaped breast implant 11 have the benefits of overcoming problems known in the art of visible, palpable, and wrinkled implant edges by creating a wedge-shaped edge and decreasing the force of gravitational pull on the implant by relocating the implant center of mass.

The implant 11 can also be used for breast lift surgery, which seeks to correct the saggy appearance of the breasts that result from gravitational pull. In these types of corrections, it is important to reposition the nipple to about an angle of 20° upward. In many cases, a breast implant is inserted to reshape the saggy breast. As such, in one embodiment, the pyramid-shaped breast implant 11 is used in association with breast lift surgery to reposition the nipple and counteract the sagginess of the breast.

Redesigned Body Implants

The design features (i.e. pyramid shape, wedge-shaped edge, footprint converging towards the underlying surface, and thin periphery with thick center) of the implant 11 can be used in designing and manufacturing implants used for augmenting the volume of various parts of the body.

In another embodiment, the body implant 11 is used for the augmentation or reshaping different parts of the body, for example, but not limited to the buttock, calf, cheeks, jaw area, testes. The body implant 11 can be used in a method similar to the method of using the pyramid-shaped breast implant 11. Also, the method of manufacturing the body implant 11 is similar to the method of manufacturing the pyramid-shaped breast implant 11.

What is claimed is:

1. A breast implant device that mimics the physical characteristics and configuration of natural fatty tissue of the breast comprising:
    a non-spherical body comprising a volume between a footprint and a front surface, the body having an upper portion and a lower portion,
    wherein the upper portion of the body is pyramid-shaped,
    wherein the front surface has a slope,
    wherein the body vertical height is unlinked to its width,
    wherein the upper portion of the body fills the breast upper pole,
    wherein the lower portion of the body is configured to fill the lower pole of the breast,
    wherein the footprint is configured to lie on a chest wall, and
    wherein a center of gravity of the body is located at the junction of the upper and lower portion of the body closer to the footprint than the front surface.

2. The breast implant device of claim 1,
    wherein the non-spherical body is constructed of a shell filled with a fill material having selective implant fill distribution,
    wherein a volume of a central palm area of the body is about 55% of a total fill volume of the body,
    wherein a volume of the upper portion is about 25% of the total fill volume of the body, and
    wherein a remaining fill volume of the total is distributed on a medial wing and a lateral wing.

3. The breast implant device of claim 2 having an alternative implant fill distribution wherein about 45% of the total fill volume is located above an implant profile line and about 55% of the total fill volume is located below the implant profile line.

4. The breast implant device of claim 2, wherein the shell is filled with a material selected from the group consisting of sterile normal saline and silicone gel.

5. The breast implant device of claim 2, wherein the volume has a fill distribution which accounts for existing native breast volume, wherein the distribution is based on a target upper volume of a breast, a target lower volume of a breast, and a total volume of the breast implant device,
    wherein the target upper volume is located above a nipple line;
    wherein the target lower volume is located below the nipple line;
    wherein the nipple line is located close to an apex of a side profile of the breast implant device;
    wherein a total volume is a volume of an implant and existing breast tissue;
    wherein the total volume is equal to the upper volume plus the lower volume; and
    wherein the total volume of the breast implant device is selected so that the upper volume is about 45% of the total volume and the lower volume is about 55% of the total volume.

6. The breast implant device of claim 2, wherein an outer surface of the shell is textured.

7. The breast implant device of claim 2, wherein an outer surface of the shell is smooth.

8. The breast implant device of claim 1, wherein the footprint has an increased thickness.

9. The breast implant device of claim 8, wherein the footprint comprises at least one of interlocking C-shapes, a cross, or a rim around a perimeter of the footprint.

10. The breast implant device of claim 2, wherein the shell has fixation holes.

11. The breast implant device of claim 2, wherein the laterally wing extends to the axilla.

12. The breast implant device of claim 1, further comprising at least one septum disposed in an interior of the body.

13. The breast implant device of claim 1,
    wherein a boundary of the footprint has a paraboloid shape,
    wherein the footprint converges towards a chest wall,
    wherein a height of the footprint is greater than a width of the footprint.

14. The breast implant device of claim 1 further comprising:
    a pre-operative implant sizer that is used to determine the body volume, height, and width.

15. The breast implant device of claim 1 further comprising:
    a tissue expander that is used to provide a surgical pocket sufficient for implanting the breast implant device.

16. The breast implant of claim 1, wherein the body volume, height, and width are adjusted for placement in other parts of the body.

* * * * *